United States Patent [19]

Baker

[11] Patent Number: 4,560,655
[45] Date of Patent: Dec. 24, 1985

[54] SERUM-FREE CELL CULTURE MEDIUM AND PROCESS FOR MAKING SAME

[75] Inventor: Paul E. Baker, Bozeman, Mont.

[73] Assignee: Immunex Corporation, Seattle, Wash.

[21] Appl. No.: 450,430

[22] Filed: Dec. 16, 1982

[51] Int. Cl.[4] .......................... C12N 5/02; C12N 5/00
[52] U.S. Cl. .................................... 435/241; 435/240
[58] Field of Search ............... 435/240, 241, 948, 244; 260/403

[56] References Cited

U.S. PATENT DOCUMENTS

| Re. 30,985 | 6/1982 | Cartaya | 435/241 |
|---|---|---|---|
| 3,887,430 | 6/1975 | Torney et al. | 435/241 |
| 4,169,761 | 10/1979 | Precausta et al. | 435/241 |
| 4,205,126 | 5/1980 | Cartaya | 435/2 |
| 4,229,541 | 10/1980 | Pearson | 435/241 |
| 4,288,546 | 9/1981 | Narasimhan et al. | 435/241 |
| 4,306,022 | 12/1981 | Kinsella et al. | 435/241 |
| 4,326,034 | 4/1982 | Peel et al. | 435/241 |
| 4,328,309 | 5/1982 | Chalmers et al. | 435/241 |

OTHER PUBLICATIONS

Pedersen, "Ultracentrifugal and Electrophoretic Studies of Fetuin", 51 Journal of Physics and Colloidal Chemistry 164, 1947.
Fisher, "Molecular Growth Requirements of Single Mammalian Cells: The Action of Fetuin in Promoting Cell Attachment to Glass," et al., 44 P. Nat'l Acad. Sci. 4, 1958.
Spiro, "Studies on Fetuin, a Glycoprotein of Fetal Serum I. Isolation, Chemical Composition, and Physiochemical Properties", 235 The Journal of Biological Chem. 2860, 1960.
Puck et al., "Mammalian Cell Growth Proteins, I. Growth Stimulation by Fetuin", 59 Proceedings of the National Academy of Science 192, 1968.
Iscove et al., 147 The Journal of Experimental Medicine 923, 1978.
Iscove et al., "Complete Replacement of Serum in Primary Cultures of Erythropoietin-Dependent Red Cell Precursors (CFU-E) by Albumin, Transferrin, Iron, Unsaturated Fatty Acid, Lecithin, and Cholesterol", 126 Experimental Cell Research 121, 1980.
Schreier et al., "Clonal Induction of Helper T Cells: Conversion of Specific Signals into Nonspecific Signals", 61 International Archives of Allergy and Applied Immunology 227 (1980).
Barnes et al., "Serum-Free Cell Culture: A Unifying Approach", 22 Cell 649, 1980.
Lehniger Biochemistry, Second Edition 1975, Worth Publishers Inc. NY, NY p. 673.
Rizzino et al., Proceedings of the National Academy of Science U.S.A. vol. 75, (1978) pp. 1844–1848.
Barnes, Cell vol. 22 Dec. 1980, pp. 649–655.
Ham et al., In Nutritional Requirements of Cultured Cells edited by H. Katsuta 1978, University Park Press Baltimore pp. 104–107.
CRC Handbook Series in Nutrition and Food 1977, Rechcigl editor vol. IV, pp. 42–43.
Barnes and Sato, "Method for Growth of Cultured Cells in Serum-Free Medium," 102 *Anal. Biochem.* 255 (1982).
Fisher and Lane, "Carbohydrate Structure of the Major Glycoprotein from Cold-Insoluble Globulin," 11 *J. Supramol Struct.*, 391–399, (1979).
Barnes and Sato, "Growth of a Human Mammary Tumor Cell Line in a Serum-Free Medium," 281 *Nature (London)* 388–389, (1979).

(List continued on next page.)

Primary Examiner—Sam Rosen
Assistant Examiner—William J. Herald
Attorney, Agent, or Firm—Christensen, O'Connor Johnson & Kindness

[57] ABSTRACT

A defined serum-free medium that is capable of growing a wide range of suspension and monolayer cells includes a serum substitute composed of fetuin, transferrin, phosphatidylcholine, e.g., 1-oleoyl-2-palmitoyl-phosphatidylcholine, linoleic acid and cholesterol. The medium also includes various inorganic salts, carbohydrates, amino acids, buffering agents, vitamins, and compounds to simulate the natural cell environment.

20 Claims, 4 Drawing Figures

OTHER PUBLICATIONS

Orly and Sato, "Fibronectin Mediates Cytokinesis and Growth of Rat Follicular Cells in Serum-Free Medium," 17 *Cell* 295-305 (1979).

Simonian et al., "Growth and Function of Cultured Bovine Adrenocortical Cells in a Serum-Free Defined Medium," 111 *Endocrinology* 919-927 (1982).

Ali et al., "Restoration of Normal Morphology, Adhesion and Cytoskeleton in Transformed Cells by Addition of a Transformation-Sensitive Surface Protein," 11 *Cell* 115-126, (1977).

Barnes et al., "Effects of a Serum Spreading Factor on Growth and Morphology of Cells in Serum-Free Medium," 14 *J. Supramol. Struc.* 47-63, (1980).

Betz and Muller, "Culture of Chick Embryo Neural Retina in Serum-Free Medium," 138 *Exp. Cell Res.* 297-302, (1982).

Bottenstein et al., "Selective Survival of Neurons from Chick Embryo Sensory Ganglionic Dissociates Utilizing Serum-Free Supplemented Medium," 125 *Exp. Cell Res.* 183-190, (1980).

Fox, "A Glossary of Essential Phospholipids, Lipids and Lipoproteins," *Phosphatidylcholine Biochemical and Clinical Aspects of the Central Phospholipids,* (New York, 1976).

SERUM-FREE CELL CULTURE MEDIUM AND PROCESS FOR MAKING SAME

TECHNICAL FIELD

The present invention relates to a cell culture medium and to a process for preparing same, and more particularly to a cell culture medium that utilizes a defined serum substitute and that is capable of growing a wide range of both suspension and monolayer cells.

BACKGROUND OF THE INVENTION

The growth of various cell lines in the laboratory is critical to pharmaceutical development, clinical practice and research investigation. The production of vaccines against various infections diseases requires the growth in liquid cultures of mass quantities of virus-producing cells. In the clinic, continuous maintenance of cells in culture is imperative for many purposes, such as clinical assessment of immune functions and tissue typing in matching donor tissue to transplantation patients. In the research laboratory, tissue culture media of various formulations are required for experimentation in neurophysiology, bacteriology, microbiology, physiology, immunology, endocrinology, biochemistry and cell biology.

The therapeutic use of various monoclonal antibodies is now beginning. To date, the vast majority of monoclonal antibody producing cell lines have been of murine origin. Although murine monoclonal antibodies can be grown to large numbers in the peritoneal cavity of normal mice, it can be safely predicted that they will be of limited therapeutic efficiency in humans who will recognize the murine antibody as a foreign protein and react against it. Similar reactions in the past have led to serum sickness and anaphylaxis. As a result, efforts are being made to develop human hybridoma monoclonal antibody-producing cell lines. Known human antibody-producing cell lines cannot be grown in mice because the animals' immune response destroys them. They could be grown in nude mice, which, since lacking a thymus, are incapable of reacting against human cell line antigens. However, the high cost of nude mice precludes their exploitation in the development of therapeutic human hybridoma cell line products. As a result, practical production of human monoclonal antibodies will require the in vitro culturing of antibody-producing cell lines, with large-scale cultures being needed for production of therapeutic quantities of the antibodies.

In the past, many of the culture requirements for different mammalian cells and tissues have been identified. For instance, it is now known that cells require various sugars, organic and inorganic salts, metal ions, amino acids and derivatives, vitamins and coenzymes, and carbohydrates. This knowledge has led to the development of various media, such as Roswell Park Memorial Institute 1640 media (hereinafter "1640"), Modified Eagles Medium (hereinafter "MEM") and Dulbecco's Modified Eagle's Medium (hereinafter "DMEM"). In addition to the chemically defined substances in these media, the growth of cells in culture has required the addition of some natural product, such as fetal calf serum (hereinafter "FCS"), to approximate a natural environment for the cell or tissue culture. The FCS is routinely used in many animal cell cultures at a 2 to 35 percent by volume concentration.

Although FCS in 1640, MEM or DMEM supports the in vitro growth of many mammalian cell types, the precise components in the serum that promote cell growth remain undefined. It is known, however, that the serum component of media creates numerous problems in the cell cultures. For example, due to variable conditions in slaughterhouses and herd health, FCS and other sera often contain undiscernible viruses which often produce disease. The viral contamination of FCS is then carried through to the final vaccine or hormone product generated by the cells grown in FCS with obvious calamitous results. For researches interested in strict control of additives to cultured cells, serum represents a source of unknown proteins, polypeptides, hormones, salts, et cetera, thus making strict determination of cell growth requirements impossible. In addition, FCS is often difficult to obtain and is expensive when available. For instance, when used at a 10 percent by volume concentration, its cost can be approximately ten times that of the collective costs of the other compounds and chemicals used in standard tissue culture media.

As a consequence of the drawbacks of the use of FCS in cell and tissue culturing, attempts have been made to develop substitutes for FCS. In one type of culture medium disclosed by Iscove, Guilbert and Weyman in 126 *Experimental Cell Research* 121 (1980) (hereinafter "Iscove's Medium") fetal calf serum was replaced with bovine serum albumin (hereinafter "BSA") human transferrin, and a mixture of phosphatidylcholines, linoleic acid and cholesterol. A severe limitation of Iscove's Medium is that it is capable of growing only a highly restricted set of cells.

Another serum-free cell culture medium is disclosed by Cartaya in U.S. Pat. Nos. 4,205,126 and Re. 30,985, wherein the medium is composed of amino acids, biotin-folic acid, thyroxine, insulin, hydrocortisone, essential fatty acids, vitamins, and surfactants.

A further serum-free medium is disclosed by Torney et al. in U.S. Pat. No. 3,887,930, which incorporates a water-soluble lipid and an ion-exchange resin. Although the ion-exchange resin is said to be beneficial for culturing monolayer cell lines, the removal of cells from the resin can be very difficult.

Thus, it is a principal object of the present invention to provide a defined, serum-free medium capable of culturing a wide range of cells both in suspension and as cell monolayers.

It is a further object of the present invention to provide a serum-free culture medium capable of growing myeloma cells to be fused to normal cells to create antibodies secreting hybridomas, of growing the resultant hybridoma cells, and of cloning the hybridoma cells.

In addition, it is an object of the present invention to provide a culture medium useful for a wide range of mammalian cell culture experimentation.

SUMMARY OF THE INVENTION

The present invention relates to a defined cell culture medium that is capable of growing a wide range of both suspension and monolayer cells and that is capable of supporting all aspects of hybridoma monoclonal antibody production, and also relates to a process for utilizing the defined medium for culturing such cells and cell lines. The medium includes a serum substitute composed of fetuin, an α-globulin fraction of normal fetal serum, and transferrin. The serum substitute also includes a defined phosphatidylcholine having the general formula:

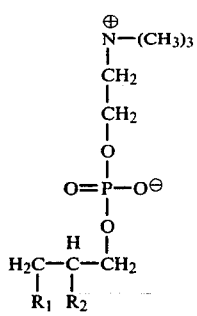

In the above formula for phosphatidylcholine, $R_1$ may be saturated fatty acid residue selected from the group consisting of lauric acid, myristic acid, palmitic acid, and stearic acid, while $R_2$ may be an unsaturated fatty acid residue selected from the group consisting of oleic acid, linoleic acid, linolenic acid and arachidonic acid. Alternatively, the positions of the $R_1$ and $R_2$ sites may be reversed.

The medium of the present invention also includes various inorganic salts, carbohydrates, amino acids, buffering agents, vitamins and compounds to simulate the natural cell environment. If desired, many of the amino acids, carbohydrates, salts, vitamins and compounds may be obtained from a commercially available synthetic medium, such as DMEM. In addition to the above-described serum substitute various additional amino acids, salts, carbohydrates, vitamins and compounds may be added to DMEM thereby to compose the complete serum-free medium of the present invention. To culture various cell lines, the medium of the present invention may be simply substituted for currently used media to promote growth of a wide range of both suspension and monolayer cells without the uncertainty of unknown components being included.

BRIEF DESCRIPTION OF THE DRAWINGS

The details of the present invention will be described in connection with the accompanying drawings, in which.

DETAILED DESCRIPTION OF THE PREFERRED EMBODIMENT

Figure 1:
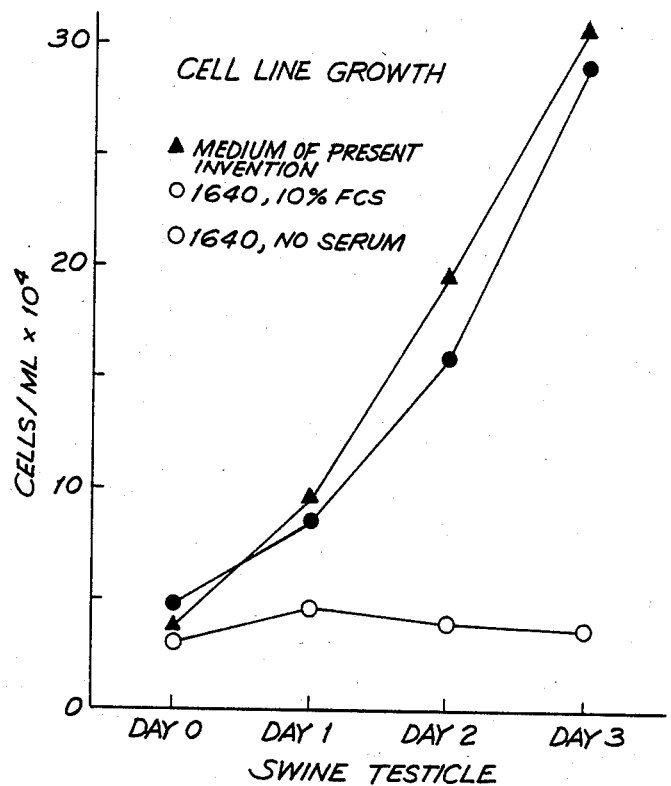
FIG. 1 is a graph illustrating the proliferation of swine testicle cells when grown in the serum-free medium of the present invention, 1640 supplemented with 10 percent by volume FCS and serum-free 1640.

In accordance with the best mode of the present invention, an improved, defined medium for the growth of cell and tissue cultures includes a serum substitute composed in basic form of fetuin, 1-oleoyl-2-palmitoyl phosphatidylcholine and transferrin. Fetuin is an α-globulin composed of polypeptides and carbohydrates and has a molecular weight of about 48,000 Daltons. It has been isolated from fetal calf serum by ammonium sulfate fractionation. Fetuin is available from many commercial sources, such as from California Biochemicals, Catalog No. 341506. In preferred quantity, approximately 9 micrograms to 1500 milligrams of fetuin may be utilized per liter of medium.

Although it is believed that fetuin does not itself cause cell growth, it may be useful in normal cellular development to maintain membrane integrity and encourage monolayer cell attachment and spreading. As discussed below, the medium of the present invention was found to support the vigorous growth of numerous monolayer cells, such as McCoys, Vero, WI38, swine testicle and human rhabdomyosarcoma. Applicant speculates that success in culturing monolayer cells with the medium of the present invention may possibly be due to fetuin's high anion binding capacity that may neutralize electrostatic repulsion between the cell surface and the substrate, as well as to its ability to serve as a protein source.

The serum substitute of the present invention also includes phosphatidylcholine as a lipid source. In the following basic structure of phosphatidylcholine:

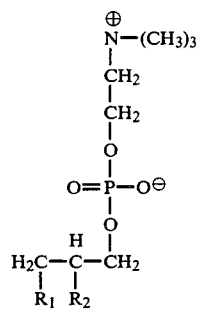

a saturated fatty acid residue of lauric acid, myristic acid, palmitic acid or stearic acid may be attached to the $R_1$ site while an unsaturated fatty acid residue of oleic acid, linoleic acid, linolenic acid and arachidonic acid may be attached to the $R_2$ site. Alternatively, one of these unsaturated fatty acids may be attached to the $R_1$ site and correspondingly, a saturated fatty acid may be attached to the $R_2$ site.

In one preferred form of the present invention, the $R_1$ site is composed of oleic acid residue and the $R_2$ site is composed of palmitic acid residue to form 1-oleoyl-2-palmitoyl-phosphatidylcholine. Applicant has found that this particular lipid compound, in addition to being totally defined, may be sonicated much more quickly into a small enough size to be usable by the cultured cells relative to the time needed to sonicate other lipid compounds, such as an undefined lecithin. 1-oleoyl-2-palmitoyl phosphatidycholine is available commercially, and preferably is utilized in concentrations of approximately 180 micrograms to 18 milligrams for each liter of medium of the present invention.

In a preferred embodiment of the present invention, various additives are added to the 1-oleoyl-2-palmitoyl phosphatidylcholine, including steroids, BSA, and other fatty acids not bound to phosphatidylcholine. Preferably, the unbound fatty acid is composed of linoleic acid in a concentration of approximately 0.007 milligrams per liter of medium, and the steroid is composed of cholesterol in a concentration of approximately 0.0193 milligrams per liter of medium. Also, preferably, the BSA is utilized in a concentration of approximately 50 milligrams per liter of medium. The 1-oleoyl-2-palmitoyl phosphatidylcholine, linoleic acid, cholesterol and BSA may be premixed together as a stock solution.

Transferrin, the third basic component of the serum substitute of the present invention, is a $\beta_1$-globulin of plasma and is capable of associating reversibly with iron and thus acts as an iron-transporting protein. Preferably, approximately from three to 300 milligrams of human transferrin are utilized per liter of medium. In preparing a stock solution, transferrin may be partially or wholly saturated with ferric choloride (FeCl$_3$.6-H$_2$O).

In addition of the above-described serum substitute, the culture medium of the present invention also includes various salts to form a balanced salt solution to maintain the proper pH and osmotic pressure in the medium and also to provide an adequate concentration of essential inorganic ions. The salts may include calcium chloride (anhydrous) (CaCl$_2$) in a preferred concentration of approximately 200 milligrams per liter of medium; ferric nitrate (Fe(NO$_3$)$_3$.9H$_2$O) at a preferred concentration of approximately 0.10 milligram per liter; potassium chloride (KCl) at a preferred concentration of approximately 400 milligrams per liter; magnesium sulfate (anhydrous) (MgSO$_4$) at a preferred concentration of approximately 97.67 milligrams per liter; sodium chloride (NaCl) at a preferred concentration of approximately 6400 milligrams per liter; sodium bicarbonate (NaHCO$_3$) at a preferred concentration of approximately 2500.0 milligrams per liter; sodium phosphate (monobasic) (NaH$_2$PO$_4$.H$_2$O) at a preferred concentration of approximately 125.0 milligrams per liter; and sodium selenite (Na$_2$SeO$_3$.5H$_2$O) at a preferred concentration of approximately 0.00224 milligrams per liter. Except for the sodium bicarbonate and sodium selenite, these salts are contained in commercially available powder formulations of high-glucose DMEM, such as from Gibco Laboratories, Catalog No. 430-2100.

The salts are balanced by an appropriate buffer. One such buffer is N-2-hydroxyethylpiperazine-N'-ethanesulphonic acid (hereinafter "HEPES") in an amount of approximately 5958.0 milligrams per liter of medium.

In addition to the salts set forth above, the cell culture medium of the present invention includes the 13 essential amino acids and several supplementary amino acids. The preferred concentrations of the essential amino acids per liter of medium include approximately 84 milligrams per liter of medium of L-arginin.HCl; approximately 28.0 milligrams per liter of L-cystine; approximately 62.57 milligrams per liter of L-cystine.2HCl; approximately 42.0 milligrams per liter of L-histidine.HCl.H$_2$O; approximately 105.0 milligrams per liter of L-isoleucine; approximately 105.0 milligrams per liter of L-leucine; approximately 146.0 milligrams per liter of L-lysine.HCl; approximately 30.0 milligrams per liter of L-methionine; approximately 66.0 milligrams per liter of L-phenylalanine; approximately 95.0 milligrams per liter of L-threonine; approximately 16.0 milligrams per liter of L-tryptophane; approximately 103.79 milligrams per liter of L-tyrosine (disodium salt), and approximately 94.0 milligrams per liter of L-valine. In addition to these essential amino acids, preferably the present invention also includes the following supplemental amino and imino acids per liter of medium: approximately 22.0 milligrams per liter of L-alanine; approximately 19.0 milligrams per liter of L-asparagine.H$_2$O; approximately 26.4 milligrams per liter of L-aspartic acid; approximately 66.0 milligrams per liter of L-glutamic acid; approximately 584.0 milligrams per liter of L-glutamine; approximately 30.0 milligrams per liter of L-glycine; approximately 35.2 milligrams per liter of L-proline, and approximately 42.0 milligrams per liter of L-serine. Except for L-alanine, L-asparagine.H$_2$O, L-aspartic acid, L-cystine, L-glutamic acid and L-proline, all of the other above-mentioned amino acids are included in commercially available, powdered, high-glucose DMEM, such as Catalog No. 430-2100 from Gibco Laboratories. As is known in the art, stock solutions of more soluble and more stable amino acids may be preprepared as well as stock solutions of less soluble amino acids, such as L-tyrosine and L-cystine that are commonly dissolved in dilute acid.

The cell culture medium of the present invention in preferred form further includes several vitamins and co-factors for cell growth and multiplication and for forming essential parts of coenzymes involved in metabolism. These vitamins and co-factors may include biotin in a concentration of approximately 0.1467 milligrams per liter of medium; D-Calcium pantothenate at a concentration of approximately 4.0 milligrams per liter; choline chloride in a concentration of approximately 4.0 milligrams per liter; folic acid in a concentration of approximately 4.0 milligrams per liter; I-Inositol at a concentration of approximately 7.2 milligrams per liter; nicotinamide in a concentration of approximately 4.0 milligrams per liter; pyridoxal.HCl in a concentration of approximately 4.0 milligrams per liter; riboflavin in a concentration of approximately 0.4 milligrams per liter; thiamine.HCl in a concentration of approximately 4.0 milligrams per liter; and vitamin B$_{12}$ at a concentration of approximately 0.1467 milligrams per liter. All of the above-identified vitamins and co-factors, except for biotin and vitamin B$_{12}$, are contained in commercially available, powdered, high-glucose DMEM, such as Catalog No. 430-2100 from Gibco Laboratories.

The cell culture medium of the present invention also ideally includes sources of carbohydrates, preferably in the form of D-glucose in a concentration of approximately 4500.0 milligrams per liter of medium. An inorganic salt, sodium pyruvate, is also contained in the medium in a concentration of approximately 96.8 milligrams per liter. The D-glucose and sodium pyruvate requirement is satisfied by the above-mentioned powdered high glucose DMEM.

The cell culture medium of the present invention in addition preferably includes approximately 15.0 milligrams per liter of phenol red as a pH indicator and approximately 11.7 milligrams per liter of 2-mercaptoethanol as a chemical additive. The phenol red is contained in commercially available, powdered, high-glucose DMEM, for instance from the source set forth above.

The defined, serum-free medium of the present invention may be prepared from stock solutions of fetuin; 1-oleoyl-2-palmitoyl phosphatidylcholine linoleic acid and cholesterol; and transferrin that are added to stock solutions of the various inorganic salts, amino acids, vitamins, co-factors, carbohydrates and buffers not above. Alternatively, the culture medium of the present invention may be formulated from stock solutions of fetuin; 1-oleoyl-2-palmitoyl phosphatidylcholine, linoleic acid and cholesterol; and transferrin together with a commercially available, synthetic medium composed of various inorganic salts, amino acids, vitamins and carbohydrates, such as high glucose DMEM. This mixture of serum substitute and synthetic medium may be supplemented with additional inorganic salts, amino acids, vitamins, co-factors and buffers to compose the complete, serum-free medium of the present invention.

The serum-free medium of the present invention has been found to promote growth of a wide variety of suspension and monolayer cell and tissue cultures as vigorously as, if not better than, the growth of the cells and tissues in a standard medium, such as 1640 or DMEM, either with or without serum supplementation. The serum-free medium of the present invention was found to promote excellent growth of the following suspension cells/cell lines:

| Cell Line | Description |
| --- | --- |
| Bovine T cells | Normal IL-2 dependent bovine T-cell lines |
| P815 | Murine mast tumor cell line |
| Jurkat | Human T-cell leukemia |
| CTLL | Murine continuous T-cell lines |
| FS6 | Murine T-cell hybridoma |
| Ag14 | Murine myeloma cell line |

In addition, the serum-free culture medium of the present invention has been found to promote the growth of a wide range of monolayer cells, such as those used in vaccine or hormone production. These cells/cell lines include:

| Cell Line | Description |
| --- | --- |
| 3T3 | Mouse fibroblast |
| Human Rhabdomyosarcoma | Human tumor cell line |
| McCoy's | Murine epithelial cells |
| L929 | Murine tumor cell line |
| HeLa | Adherent human carcinoma cell line |
| Vero | African green monkey kidney |
| WI38 | Human foreskin fibroblast cell line |
| Swine testicle | Porcine cell line |
| Bovine turbinate | Bovine endothelial cell line |

The ability of the serum-free medium of the present invention to promote growth of the above cell lines was tested by culturing the cell lines in the medium of the present invention, in 1640 Medium supplemented with ten percent FCS and serum-free 1640 Medium. The cells were seeded at low density in replicate cultures in the presence of one of the above media. After each day of incubation, the replicate cultures were monitored for viable cell concentration. For all of the cell lines noted above, the cultures conducted in the serum-free medium of the present invention grew as well or better than and reached as high a saturation density as identical cultures in serum-supplemented or serum free 1640. The results of the growth tests on the swine testicle and Ag14 cell lines are set forth in FIGS. 1 and 2. The above cell lines were also tested for prolonged growth in the serum-free medium of the present invention and have been cultured for at least several months.

Cellular proliferation was also tested biochemically by determining the rate of cellular replication by incorporation of radiolabelled nucleic acid precursor $^3$H-Tdr into replicating DNA. Cells were seeded at low density in replicate microwell cultures in the presence of either the serum-free medium of the present invention, 1640 supplemented with ten percent FCS or serum-free 1640. After each day of incubation, the replicate cultures were pulsed for four hours with $^3$H-Tdr which, when incorporated into the DNA of replicating cells, provides a quantitative index as to the rate at which cells are proliferating in various media. Cellular incorporation of $^3$H-Tdr was monitored by scintillation counting, thereby providing a reproducible measure of cell growth.

Figure 3:
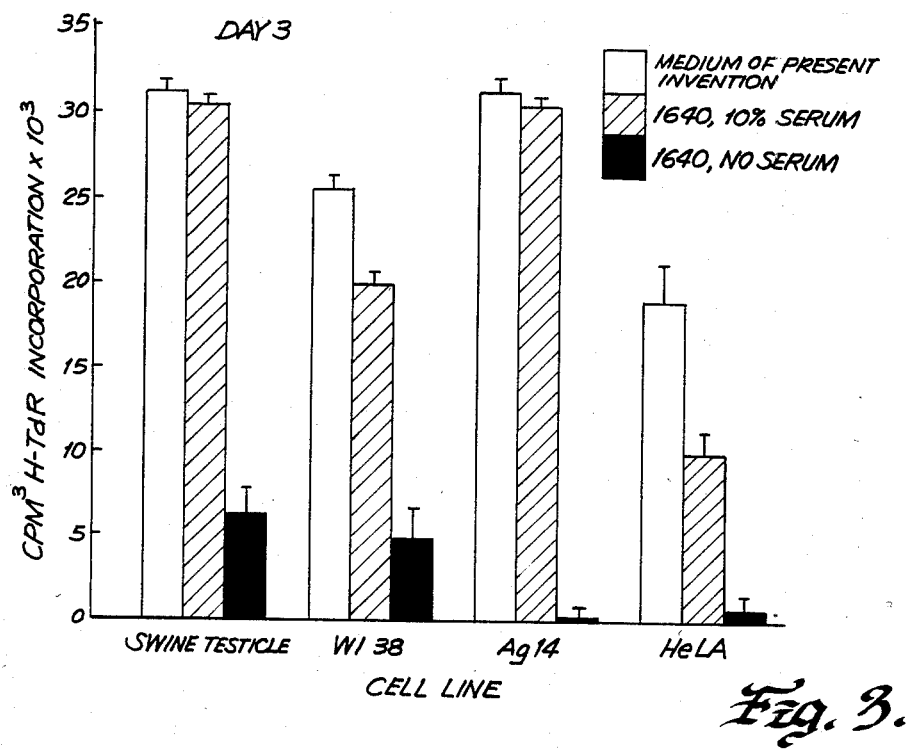
FIG. 3 is a graph illustrating cellular proliferation of various cell lines as determined by the quantity of incorporation of radiolabeled nucleic acid precursor, tritiated thymidine (hereinafter "3H-Tdr") into replicating DNA and quantified by counts per minute (CPM), utilizing the serum-free medium of the present invention, 1640 supplemented with 10 percent by volume FCS and serum-free 1640.

The results of the tests on the Swine Testicle, WI38, Ag14, and HeLa cell lines are shown in FIG. 3, in terms of CPM of $^3$H-Tdr incorporation at day three from replicate cultures (inoculum density of $5 \times 10^4$ cells per milliliter). As evident from FIG. 3, the serum-free medium of the present invention supported cell growth at least as well as did 1640 supplemented with ten percent FCS. The serum-free 1640 supported little, if any, cellular proliferation.

Tests have confirmed that the serum-free medium of the present invention was capable of supporting the fusion of Ag14 myeloma cells with normal spleen cells to create antibody-secreting hybridomas. Studies also have found that such antibody-secreting hybridomas can be maintained at least as well in the serum-free medium of the present invention as in serum-supplemented cultures.

In addition, applicant has found that the resulting hybridoma cells can be cloned in the serum-free medium of the present invention. These results confirm that the serum-free medium of the present invention is suitable for all aspects of hybridoma technology from fusion to log-phase growth of antibody-secreting hybrids to cloning and stabilization of such hybrids.

The serum-free medium of the present invention also has been found to be useful in immunological experimentation, particularly those associated with tissue typing. Traditional tissue typing is routinely conducted by assessment of MLR. When lymphocytes from one individual are cultured with histoincompatible lymphocytes, the responding cells become transformed into large blast cells which replicate DNA. MLR responses are commonly assayed by $^3$H-Tdr incorporation as a function of time and by the generation of reactive cytolytic T-cells (CTL). When cultured with histocompatible leucocytes, no MLR reactivity occurs. Thus, the MLR is a test for histocompatibility.

Figure 4:
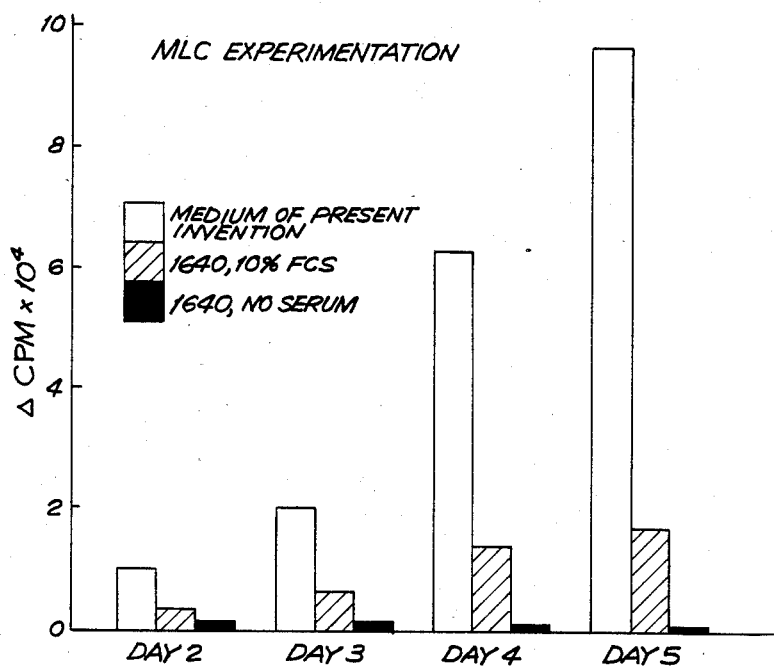
FIG. 4 is a bar graph illustrating the capacity of the serum-free medium of the present invention to promote mixed lymphocyte reactivity (MLR) in relation to the ability of 1640 supplemented with 10 percent by volume FCS and of serum-free 1640 to promote the same reactivity.

The capacity of the serum-free medium of the present invention to promote MLR in both murine and human lymphocyte systems was tested. Reactivity in both systems was assessed by measurement of cellular proliferation ($^3$H-Tdr incorporation) as a function of time and also by generation of reactive CTL, as is well known in the art. Such studies were conducted by utilizing the serum-free medium of the present invention, by 1640-supplemented with ten percent FCS and by serum-free 1640. As shown in FIG. 4, the serum-free medium of the present invention supported MLR reactivity to a greater degree than did identical cultures conducted in FCS-supplemented or serum-free 1640. Furthermore, more potent CTL responses were observed following MLR reactions in the serum-free medium of the present invention than in standard serim-containing cultures. As also shown in FIG. 4, MLR experimentation conducted in standard 1640 medium in the absence of serum was totally unsuccessful.

EXAMPLE I

Preparation of Serum Substitute

The serum substitute utilized in the medium of the present invention may be formulated in the following stock solutions:

Stock Solution 1—Fetuin 16.5 grams of fetuin obtained from Cal Biochem-Behring Corporation, LaJolla, Calif., (hereinafter "Cal-Bio"), Catalog No. 341506, is dissolved in 500 ml of sterilized water. This solution may be stored at 4° C. for several days and is sufficient for 100 one-liter volumes of cell culture medium.

Stock Solution 2—Lipid

A solution of filler medium is prepared by combining approximately 225 ml of unbuffered and sterile filtered DMEM with 25 ml of 20 percent fatty acid-free bovine serum albumin (Sigma, Catalog No. A7511) which as been filter-sterilized in water. A second solution is formed by adding 7.00 mg of linoleic acid (Sigma, Catalog No. L1376) and approximately 19.33 mg of cholesterol (Sigma, Cataog No. CH-S) to 100 ml of 1-oleoyl-2-palmitoyl phosphatidylcholine (20 mg/ml in chloroform) (Avanti Polar Lipids, 2421 High Bluff Road, Birmingham, Ala.) and then mixing thoroughly. This is to be performed at 4° C. in a nitrogen gas glove box, since linoleic acid and 1-oleoyl-2-palmitoyl phosphatidylcholine are easily oxidized. Next, the mixture is dispensed into 10 ml aliquots into sterile glass tubes, sealed tightly and stored at −80° C. Sufficient amounts of the two solutions exist for 1000 one-liter quantities of cell culture medium.

Prior to preparation of this portion of the serum substitute, the contents of one test tube of the lipid solution is poured into a 250 ml beaker and then evaporated under nitrogen gas at room temperature. 250 ml of the first solution (filler medium) are added to the beaker and then the contents sonicated at 80 watts for five to ten minutes in an ice bath, optimally with a two-centimeter diameter probe that has been sterilized with 70 percent ethyl alcohol. The resulting stock solution may be stored at 4° C. for several days if the container is kept tightly capped. Enough lipid stock solution is produced for 100 one-liter volumes of cell culture medium.

Stock Solution 3⅓ Iron Saturated Transferrin

A first, transferrin solution is produced by dissolving by constant stirring 3.18 g of human transferrin (Cal-Bio, Catalog No. 547904) in 35.0 ml of unbuffered DMEM which has been sterile filtered. A second, iron solution is formed by dissolving 180 mg of ferric chloride ($FeCl_3.6H_2O$) in 10 ml of filter-sterilized water by constant stirring. This iron solution can be stored for prolonged periods of time.

The two solutions are combined by mixing 35.0 ml of the transferrin solution with 350 microliters of the iron solution. Once the resulting solution is filter sterilized, it can be stored at 4° C. for at least one month. The resulting solution is adequate for 100 one-liter volumes of cell culture medium.

EXAMPLE II

Complete Serum-Free Medium and First Method of Preparing Same

The serum-free cell culture medium of the present invention is prepared from the serum substitute set forth in Example I together with the standard powdered, high-glucose DMEM and various organic salts, amino acids, vitamins, co-factors and other components. The complete medium is initially prepared as a series of stock solutions in addition to stock solutions 1, 2, and 3 in Example I. The stock solutions are then combined immediately before the medium is used. The use of stock solutions prevents undesirable degradation of various substances, separates easily soluble from less soluble components and permits labile components to be maintained in more stable condition than if mixed with other components.

The constituents of procedures for making DMEM are set forth in:

1. Dulbecco and Freeman, 8 *Virology* 396 (1959);
2. Smith, Freeman, Vogt and Dulbecco, 12 *Virology* 185 (1960); and
3. Tissue Culture Standards Committee, *In Vitro*, Volume 6, No. 2, page 93.

The components of powdered, high-glucose DMEM as marketed by Gibco Laboratories under Catalog No. 430-2100 is set forth below as Table I.

TABLE I

| Powder, High-Glucose DMEM | |
|---|---|
| Component | Amount (Mg/Liter of Medium) |
| *Salts* | |
| $CaCl_2$ (anhyd.) | 200.00 |
| $Fe(NO_3)_3.9H_2O$ | 0.10 |
| KCl | 400.00 |
| $MgSO_4$ (anhyd.) | 97.67 |
| NaCl | 6400.00 |
| $NaH_2PO_4.H_2O$ | 125.00 |
| *Other Components* | |
| D-Glucose | 4500.00 |
| Phenol red | 15.00 |
| *Amino Acids* | |
| L-Arginine.HCl | 84.00 |
| L-Cystine.2HCl | 62.57 |
| L-Glutamine | 584.00 |
| Glycine | 30.00 |
| L-Histidine.HCl.$H_2O$ | 42.00 |
| L-Isoleucine | 105.00 |
| L-Leucine | 105.00 |
| L-Lysine.HCl | 146.00 |
| L-Methionine | 30.00 |
| L-Phenylalanine | 66.00 |
| L-Serine | 42.00 |
| L-Threonine | 95.00 |
| L-Tryptophane | 16.00 |
| L-Tyrosine (Disodium salt) | 103.79 |
| L-Valine | 94.00 |
| *Vitamins* | |
| D-Calcium pantothenate | 4.00 |
| Choline chloride | 4.00 |
| Folic acid | 4.00 |
| I-Inositol | 7.20 |
| Nicotinamide | 4.00 |
| Pyridoxal HCl | 4.00 |
| Riboflavine | 0.40 |
| Thiamine HCl | 4.00 |

In addition to stock solutions 1, 2, and 3 of Example I, the following stock solutions are also prepared:

Stock Solution No. 4—Amino Acid/Biotin-Vitamin $B_{12}$ Solution

A first, amino acid solution is formed by dissolving the following L-amino acids in approximately 880 milliliters of water by constant stirring at room temperature or under gentle heat: 2.20 gm of L-alanine (Sigma, Cat. No. A7627); 1.90 gm of L-asparagine (Sigma, Cat. No. A0884); 2.64 gm of L-aspartic acid (Sigma, Cat. No. A9256); 6.60 gm glutamic acid (Sigma, Cat. No. G1251); 3.52 gm proline (Sigma, Cat. No. PO380); and 9.68 gm sodium pyruvate (Gibco, Cat. No. 890-1840). A second solution (biotin-$B_{12}$ solution) is formed by dissolving the following components at 37° to 40° Celsius with constant stirring: 50 mg of biotin (Sigma, Cat. No. B4501); 50 mg of vitamin $B_{12}$ (Sigma, Cat. No. V2876); 10 microliters of 1M hydrochloric acid, and 20 ml of water. The amino acid/biotin-$B_{12}$ stock solution is formed from the two solutions by mixing the 880 ml of the first, amino acid solution with 5.8 ml of the second, biotin-$B_{12}$ solution. This produces a sufficient amount of stock solution No. 4 to form 100 one-liter volumes of culture medium. This stock solution should be stored at 4° C. and used within five days.

Stock Solution No. 5—Cystine-Hydrochloric Acid Solution 100 ml of hydrochloric acid (37%) are mixed with 3900 ml of water. 28.0 gm of cystine (Sigma, Cat. No. C8755) are added to the mixture and dissolved at room temperature by constant stirring. The resulting mixture is filter sterilized after the cystine has been totally dissolved. This subsolution can be stored several months at 4° C. and makes a sufficient amount of subsolution for 1000 one-liter volumes of cell culture medium.

Stock Solution No. 6—Sodium Selenite Solution 2.8 mg of $Na_2SeO_3$ (Sigma, Cat. No. S1382) are dissolved in 1000 ml of water by constant stirring. The resulting solution is filter sterilized with a 0.20 micron filter. The resulting stock solution is sufficient for 1250 one-liter volumes of cell culture medium and can be stored at 4° C. for several months.

Stock Solution No. 7—2-Mercaptoethanol Solution (0.1M)

3.5 ml of 0.1M 2-mercaptoethanol (Sigma, Cat. No. M6250) are mixed with 500 ml of water and filter sterilized with a 0.20 micron filter. The resulting solution is sufficient for 1000 one-liter volumes of cell culture medium and can be stored for several months at 4° C.

Stock Solution No. 8—1M HEPES Solution 2.383 kg of HEPES are dissolved in 9.5 liters of water and pH adjusted with 10M sodium hydroxide to pH 7.0 to 7.1. The solution is filter sterilized and then can be stored at 4° C. up to several months. This process produces enough stock solution No. 8 to produce 400 one-liter volumes of cell culture medium.

The water utilized in all stock solutions must be freshly prepared. The water is to be passed through a 0.20 micron filter and an ion exchange filter so that the resulting water has 10 to 18 megohm resistance (hereinafter "DDH$_2$O"). The prepared water is to be handled for only a minimum of time in polymer containers.

Preparation of Medium

One hundred liters of cell culture medium are made up from DMEM and the above stock solutions by first emptying the contents of two 50-liter packages of DMEM (Gibco, Cat. No. 430-2100) into an appropriate vessel and then adding about 90 to 95 liters of DDH$_2$O. Thereafter, the following components and stock solutions are added and thoroughly mixed at 4° C.:

A. 250 gms of sodium bicarbonate $NaHCO_3$;
B. 500 ml of stock solution No. 1 (fetuin);
C. 250 ml of stock solution No. 2 (lipid);
D. 35 ml of stock solution No. 3 ($\frac{1}{3}$ iron-saturated transferrin);
E. 880 ml of stock solution No. 4 (amino acid/biotin-$B_{12}$ solution);
F. 400 ml of stock solution No. 5 (cystine.HCl solution);
G. 80 ml of stock solution No. 6 ($Na_2SeO_3$);
H. 50 ml of stock solution No. 7 (2 Me/solution); and
I. 2.5 liters of stock solution 8 (1M HEPES, pH 7.0).

Next, the osmolarity of the medium is adjusted to 300 mOsM (±3%) by adding DDH$_2$O. The pH of the medium is adjusted to 7.1 by adding sodium hydroxide solution or HCl solution as necessary. Thereafter, the medium is filter sterilized with a 0.22 micron filter, dispensed in sterile bottles, and then stored at −80° C. To use the medium, it is thawed and then additional 2.0 mM L-glutanine is added. Standard antibiotics, such as 50 units per milliliter of penicillin and 50 micrograms per milliliter of streptomycin, can be added to the medium without deleteriously affecting the performance of the medium.

EXAMPLE III

Complete Serum-Free Medium and Second Method of Preparing Same

The serum-free cell culture medium of the present invention may be prepared from a powdered component and a frozen liquid component. The powdered component may be packaged in an appropriate quantity to make a desired volume of culture medium. The volume of the liquid component may be sized to match the quantity of the of the powdered component.

The powdered component is prepared from the "dry" ingredients set forth below in Table II, with the amounts specified in terms of grams of ingredients for 100 liters of culture medium. The ingredients may be stored together in an appropriate container or package.

TABLE II

| POWERED COMPONENTS | |
|---|---|
| COMPONENT | AMOUNT (gm/100 liter of Medium) |
| CaCl$_2$ (anhyd.) | 18.0 |
| Fe(NO$_3$)$_3$.9H$_2$O | 0.009 |
| KCl | 36.0 |
| MgSO$_4$ (anhyd.) | 8.79 |
| NaCl | 57.60 |
| NaH$_2$PO$_4$.H$_2$O | 11.25 |
| D-Glucose | 40.5 |
| Phenol red | 1.35 |
| L-Arginine.HCl | 7.56 |
| L-Cystine.2HCl | 5.631 |
| L-Glutamine | 52.56 |
| Glycine | 2.70 |
| L-Histindine.HCl.H$_2$O | 3.78 |
| L-Isoleucine | 9.45 |
| L-Leucine | 9.45 |
| L-Lysine.HCl | 13.14 |
| L-Methionine | 2.70 |
| L-Phenylalanine | 5.94 |
| L-Serine | 3.78 |
| L-Threonine | 8.55 |
| L-Tryptophane | 1.44 |
| L-Tyrosine (Disodium salt) | 9.34 |
| L-Valine | 8.46 |
| D-Calcium pantothenate | 0.36 |
| Choline chloride | 0.36 |
| Folic acid | 0.36 |
| I-Inositol | 0.648 |
| Nicotinamide | 0.36 |
| Pyridoxal.HCl | 0.36 |

TABLE II-continued

POWERED COMPONENTS

| COMPONENT | AMOUNT (gm/100 liter of Medium) |
| --- | --- |
| Riboflavin | 0.0036 |
| Thiamine.HCl | 0.36 |
| L-Alanine | 2.20 |
| L-Asparagine | 1.90 |
| L-Aspartic acid | 2.60 |
| Glutamic acid | 6.60 |
| Proline | 3.50 |
| Sodium pyruvate | 9.70 |
| HEPES | 536.2 |
| Sodium Bicarbonate | 225.0 |

The liquid component of the cell culture medium is composed of the stock solutions set forth in Examples I and II above, with the exception that stock solution No. 4 in Example II is replaced with a stock solution No. 4a which does not include the amino acids of stock solution number 4, as described more fully below. In addition, stock solution No. 8 (1M HEPES solution) has been replaced with a powder component as set forth in TABLE II above.

Stock solution No. 4a is formed by dissolving the following components at 37° to 40° C. with constant stirring: 50 mg of biotin (Sigma, Cat. No. B4501); 50 mg of vitamin $B_{12}$ (Sigma, Cat. No. V2876); 10 microliters of 1M of hydrochloric acid and 20 ml of water. This produces a sufficient amount of stock solution No. 4a to form 100 liters of culture medium. This stock solution should be stored in 4° C. and used within five days.

The components of the liquid portion of the stock solution are set forth below in TABLE III:

TABLE III

| COMPONENT | AMOUNT (ml/100 liters of Medium) |
| --- | --- |
| Fetuin (Stock Solution No. 1) | 450.0 |
| Lipid (Stock Solution No. 2) | 225.0 |
| ⅓-Iron Saturated Human Transferin (Stock Solution No. 3) | 318.0 |
| Biotin/Vitamin $B_{12}$ (Stock Solution No. 4a) | 5.87 |
| cystine - Hydrochloric Acid Solution (Stock Solution No. 5) | 360.0 |
| Sodium Selenite Solution (Stock Solution No. 6) | 72.0 |
| 2-Mercaptoethanol (Stock Solution No. 7) | 45.0 |

To the above liquid components set forth in TABLE III is added an additional 100 milliliters of 200 mM L-glutamine solution prepared by dissolving 29.2 gm of L-glutamine in 100 ml of $DDH_2O$. After being mixed together, the entire liquid component is filtered through a 0.20 uM filter and frozen at $-20°$ C. or lower until use.

To prepare the cell culture medium of the present invention, the above-described powder and liquid components are mixed together in an appropriate vessel. Next, the osmolarity of the medium is adjusted to 300 mOsM (plus or minus 3%) by adding $DDH_2O$. The pH of the medium is adjusted to 7.1 by adding sodium hydroxide solution or HCl solution as necessary. Standard antibiotics, such as 50 units per milliliter of penicillin and 50 micrograms per milliliter of streptomycin, may be added to the medium without affecting the performance of the medium.

EXAMPLE IV

Culture of Swine Testicle Cells

Comparative cultures of swine testicle cells, an adherent cell type, were conducted to ascertain the effectiveness of the medium of the present invention relative to FCS Supplemented and unsupplemented 1640 to promote growth of this type of cell. At day 0, the swine testicle cells at a concentration of $5 \times 10^4$ cells per milliliter were placed in culture in either the medium of the present invention or 1640 supplemented with ten percent FCS (by volume), 50 units per milliliter of penicillin, 50 micrograms per milliliter of gentamicin and 300 micrograms per milliliter of fresh L-glutamine. Additional cultures were initiated in 1640 supplemented with all the above-noted additives except the serum component. On days 1, 2, and 3 of culture, 0.5 milliliter samples of each culture were harvested and viable cell concentration determined. As set forth in FIG. 1, cells seeded either in the medium of the present invention or 1640 supplemented with serum, proliferated rapidly and grew to a concentration of approximately $3 \times 10^5$ cells per milliliter by day 3. Conversely, cells seeded in 1640 in the absence of serum mediated no observable growth.

EXAMPLE V

Culture of AG14 Myeloma Cells

Figure 2:
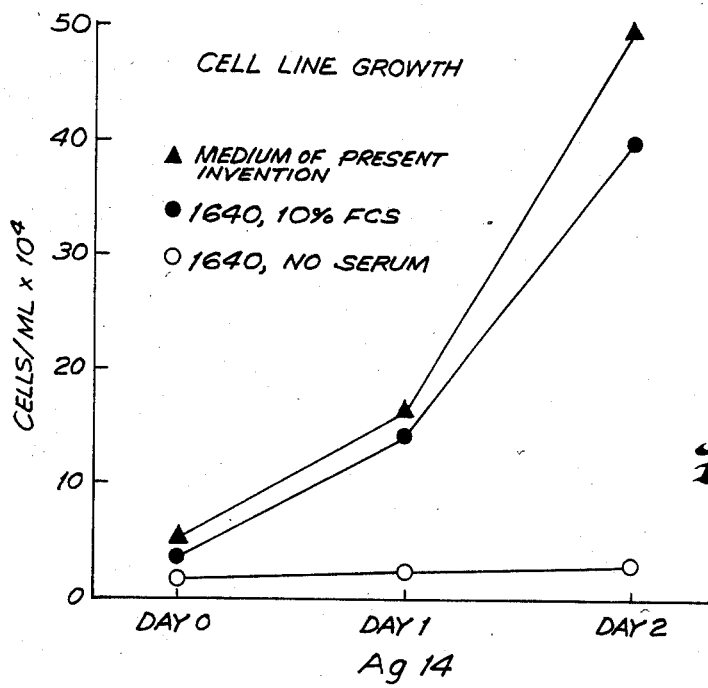
FIG. 2 is a graph illustrating the proliferation of Ag14 cells in the presence of the serum-free medium of the present invention, 1640 supplemented with 10 percent by volume FCS and serum-free 1640.

The medium of the present invention was tested for its ability to promote growth of AG14 myeloma cells, which is a suspension cell line commonly used for generation of monoclonal antibodies. Identical numbers of AG14 cells at a concentration of $5 \times 10^4$ cells per milliliter were placed in culture in day 1 in the medium of the present invention and also in 1640 supplemented with ten percent by volume FCS, 50 units per milliliter of penicillin, 50 micrograms per milliliter of gentamicin, and 300 micrograms per milliliter of fresh L-glutamine. In addition, identical cultures of the AG14 cells were conducted in 1640 supplemented with all of the above-noted additives except the FCS. As shown in FIG. 2, by day 2, cells seeded in either the medium of the present invention or serum-supplemented 1640 grew to densities in excess of $5 \times 10^5$ cells per milliliter. However, cells cultured in 1640 in the absence of serum mediated no observable growth.

EXAMPLE VI

Comparative Cellular Proliferation Monitored Biochemically

Cellular proliferation of various cell lines utilizing the culture medium of the present invention, FCS-supplemented 1640, and unsupplemented 1640, were tested biochemically by determining the rate of cellular replication by incorporation of $^3H$-Tdr. Swine testicle, WI3B (human adherent epidermal fibroblast cells), AG14 and HeLa (human uterine carcinoma cells) were placed in microplate cultures at a concentration of $5 \times 10^3$ cells per milliliter on day 0. Identical cultures were conducted in either the medium of the present invention, 1640 supplemented with ten percent by volume FCS, 50 micrograms per milliliter of gentamicin, 50 units per milliliter of penicillin, and 300 micrograms per milliliter of fresh L-glutamine. Identical cultures were also set up in the presence of 1640 together with all of the same additives except for the FCS. After three days of incubation at 37° Celsius in a humidified atmosphere of five percent carbon dioxide in air, each microculture well was pulsed with 0.5 microcurie of $^3$H-Tdr.

The cells that were proliferating in the presence of the different media would be expected to incorporate $^3$H-Tdr into replicating DNA. This DNA, once extracted, could be assessed for radioactivity by liquid scintillation counting. The larger the number of proliferating cells, the higher the CPM would be expected from harvested, cultured DNA.

After the microculture wells were pulsed with $^3$H-Tdr for four hours, all the cultures were harvested onto glass fiber strips with the aid of a multiple, automated sample harvester (Microbiological Associates, Rockville, MD). This machine harvests cultures and automatically extracts radio-labelled DNA onto glass fiber filter strips. These filter strips were then cut and each culture strip counted by liquid scintillation technique. As illustrated in FIG. 3, cultures conducted in the absence of serum resulted in minimal counts of $^3$H-Tdr incorporation into replicating cell DNA. However, cells cultured in the medium of the present invention or in 1640 supplemented with FCS and the other additives, incorporated significant amounts of $^3$H-Tdr. This serves to further document the capacity of the medium of the present invention to support cell growth at an equal or greater extent than that observed in serum-supplemented tissue culture medium.

EXAMPLE VII

Mixed Lymphocyte Reaction

The ability of the medium of the present invention to support immunological reactions in vitro (mixed lymphocyte or MLC reaction) was also investigated. Spleen cells were harvested on day 1 from C57B6 mice and placed in two-milliliter cultures in either: the medium of the present invention; 1640 supplemented with ten percent high-volume FCS, 50 units per milliliter of penicillin, 50 micrograms per milliliter of gentamicin and 300 micrograms per milliliter of fresh L-glutamine; or 1640 supplemented with the same additives with the exception of FCS. Each two-milliliter cell culture then received an equal volume of allogeneic BALB/c spleenocytes whose replication had previously been blocked by mitoylin-C (Sigma Chemical Corporation, St. Louis, MO).

In a mixed lymphocyte reaction, such as the one detailed above, antigens present on the allogeneic spleenocytes trigger replication of responder C57B6 spleenocytes. Proliferation of such spleenocytes is then assessed by a four-hour pulse with $^3$H-Tdr at days 2, 3, 4, and 5 of culture. Success of this immunological reaction is then determined by harvest of replicate cultures on the days indicated and assessment of incorporation of the $^3$H-Tdr into replicating DNA by liquid scintillation counting. As shown in FIG. 4, by this procedure, the medium of the present invention was found to support MLC stimulation to a greater extent than did 1640 supplemented with serum, penicillin, gentamicin, and glutamine. As has been the case in the previous examples, cultures conducted in the absence of serum failed.

As will be apparent to those skilled in the art to which the invention is addressed, the present invention may be embodied in particular compositions other than those specifically herein disclosed, without departing from the spirit or the essential characteristics of the invention. The particular embodiments of the serum-free medium of the present invention, described above, are therefore to be considered in all respects as illustrative and not restrictive; the scope of the present invention is as set forth in the appended claims, rather than being limited to the examples of the present invention set forth in the foregoing description.

The embodiments of the invention in which an exclusive property or privilege is claimed are defined as follows:

1. A substitute for serum in cell culture media capable of long-term culture of suspension and monolayer cells and hybridoma cells and capable of supporting fusion of cells to form hybridomas, comprising fetuin, transferrin, albumin, cholesterol and phosphatidylcholine having the general formula:

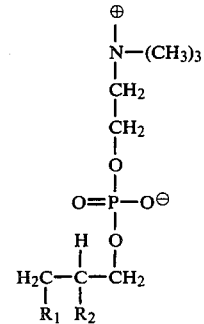

wherein $R_1$ is a saturated fatty acid residue derived from the group consisting of lauric acid, myristic acid, palmitic acid and stearic acid; and, $R_2$ is an unsaturated fatty acid residue derived from the group consisting of oleic acid, linoleic acid, linolenic acid, and arachidonic acid; or $R_1$ is an unsaturated fatty acid residue derived from the group consisting of oleic acid, linoleic acid, linolenic acid, and arachidonic acid; and, $R_2$ is a saturated fatty acid residue derived from the group consisting of lauric acid, myristic acid, palmitic acid and stearic acid; and, $R_1$ and $R_2$ are chemically bonded to the respective carbon atoms of the phosphatidylcholine.

2. The serum substitute according to claim 1, wherein the transferrin is partially to fully iron saturated by addition of up to 1.89 milligrams per liter of ferric chloride.

3. The serum substitute according to claim 1, wherein $R_1$ is derived from oleic acid and $R_2$ is derived from palmitic acid.

4. The serum substitute of claim 2, wherein the concentration of transferrin is in the range of about 3 to 300 milligrams per liter of medium, the concentration of fetuin is in the range of about 9 micrograms to 1500 milligrams per liter of medium and the concentration of defined phosphatidylcholine is in the range of about 180 micrograms to 18 milligrams per liter of medium.

5. In cell culture media capable of long-term growth of suspension cells, monolayer cells and hybridoma cells, and capable of fostering the fusion of cells to form hybridomas, such media including salts, amino acids, carbohydrates, albumin, at least one steroid and unbound fatty acid, the improvement comprising the addition of fetuin, transferrin and phosphatidylcholine having the general formula:

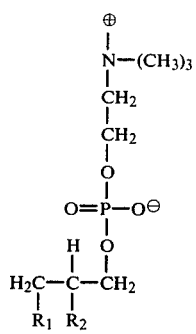

wherein:

R₁ is an unsaturated fatty acid residue derived from the group consisting of oleic acid, linoleic acid, linolenic acid, and arachidonic acid; and, R₂ is a saturated fatty acid residue derived from the group consisting of lauric acid, myristic acid, palmitic acid and stearic acid; or, R₁ is a saturated fatty acid residue derived from the group consisting of lauric acid, myristic acid, palmitic acid, and stearic acid; and, R₂ is an unsaturated fatty acid residue derived from the group consisting of oleic acid, linoleic acid, and arachidonic acid; and, R₁ and R₂ are chemically bonded to their respective carbon atoms of the phosphatidylcholine.

6. The cell culture media according to claim 5, wherein the transferrin is partially to fully iron saturated by addition of up to 1.89 milligrams per liter of ferric chloride.

7. The cell culture media according to claim 5, wherein R₁ is derived from oleic acid and R₂ is derived from palmitic acid.

8. The cell culture media according to claim 5 wherein the amino acids are selected from the group consisting of L-alanine, L-asparagine, L-arginine.HCL, L-aspartic acid, L-cystine, L-cystine 2HCl, L-glutamic acid, L-glutamine, glycine, L-histidine.HCl.H₂O, L-isoleucine, L-leucine, L-lysine.HCl, L-methionine, L-phenylalanine, L-proline, L-serine, L-threonine, L-tryptophane, L-tyrosine (disodium salt) and L-valine.

9. The cell culture media according to claim 5, wherein the salts are selected from the group consisting of calcium chloride, ferric nitrate, potassium chloride, magnesium sulfate, sodium chloride, sodium bicarbonate, sodium phosphate (monobasic), sodium selenite and sodium pyruvate.

10. The cell culture media according to claim 5, wherein the carbohydrate includes D-glucose.

11. The cell culture media according to claim 5, further comprising vitamins and cofactors selected from the group consisting of biotin, D-calcium pantothenate, choline chloride, folic acid, I-inositol, nicotinamide, pyridoxal HCl, riboflavin, thiamine.HCl, and vitamin B₁₂.

12. The cell culture media of claim 5, wherein the concentration of fetuin is in the range of about 9 micrograms to 1500 milligrams per liter of medium, the concentration of transferrin is in the range of about 3 to 300 milligrams per liter of medium and the concentration of defined phosphatidylcholine is in the range of about 180 micrograms to 18 milligrams per liter of medium.

13. In cell culture media capable of culturing suspension cells, monolayer cells and hybridoma cells are capable of supporting fusion of cells to form hybridomas, the media including Dulbecco's Modified Eagle Medium, the improvement further including in the cell culture media fetuin, partially to fully iron saturated transferrin, and phosphatidylcholine having the general formula:

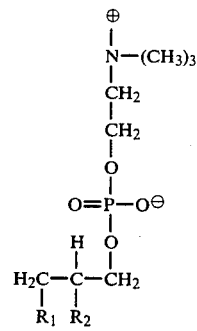

wherein:

R₁ is an unsaturated fatty acid residue derived from the group consisting of oleic acid, linoleic acid, linolenic acid, or arachidonic acid; and, R₂ is a saturated fatty acid residue derived from the group consisting of lauric acid, myristic acid, palmitic acid or stearic acid; or conversely, R₁ is a saturated fatty acid residue derived from the group consisting of lauric acid, myristic acid, palmitic acid and stearic acid; and, R₂ is an unsaturated fatty acid residue derived from the group consisting of oleic acid, linoleic acid, linolenic acid, and arachidonic acid; and, R₁ and R₂ are chemically bonded to their respective carbon atoms of the phosphatidylcholine.

14. The cell culture media according to claim 13, wherein R₁ is derived from oleic acid and R₂ is derived from palmitic acid.

15. The cell culture media according to claim 13, further comprising one or more amino acids selected from the group consisting of L-alanine, L-aspargine, L-aspartic acid, L-cystine, L-glutamic acid, and L-proline.

16. The cell culture media according to claim 13, further comprising additional amounts of D-glucose.

17. The cell culture media according to claim 13, further comprising additional amounts of organic and/or inorganic salts selected from the group consisting of sodium bicarbonate, sodium selenite, and sodium pyruvate.

18. The cell culture media according to claim 13, further comprising additional amounts of vitamins and cofactors selected from the group consisting of biotin and vitamin B₁₂.

19. The cell culture media according to claim 13, wherein the concentration of fetuin is in the range of about 9 micrograms to 1500 milligrams per liter of medium, the concentration of transferrin is in the range of about 3 to 300 milligrams per liter of medium and the concentration of defined phosphatidylcholine is in the range of about 180 micrograms to 18 milligrams per liter of medium.

20. An improved process for culturing suspension, monolayer and hybridoma cells and fusing cells to form hybridoma cells comprising the step of growing the cells in a culture medium comprising salts, amino acids, carbohydrates, albumin, one or more steroids, unbound fatty acids, fetuin in the range of about 9 micrograms to 1500 milligrams per liter of medium, transferrin in the range of about 3 milligrams to 300 milligrams per liter of medium and a defined phosphatidylcholine selected from the group consisting of 1-palmitoyl-2-oleoyl phosphatidylcholine and 1-oleoyl-2-palmitoyl phosphatidylcholine, wherein such defined phosphatidylcholine is in the range of about 180 micrograms to 18 milligrams per liter of medium.

* * * * *

UNITED STATES PATENT AND TRADEMARK OFFICE
CERTIFICATE OF CORRECTION

PATENT NO. : 4,560,655  Page 1 of 4
DATED : December 24, 1985
INVENTOR(S) : Paul E. Baker It is certified that error appears in the above-identified patent and that said Letters Patent is hereby corrected as shown below:

Page 1, line 38, "Method" should be --Methods-- (Other Publications Section)

Page 2, line 13, "Struc." should be --Struct.-- (Other Publications Section)

Column 1, line 16, "infections" should be --infectious--

Column 2, line 12, "researches" should be --researchers--

Column 5, line 24, "choloride" should be --chloride-- lines 24 & 25, "($FeCl_3 \cdot 6H_2O$)" should be --($FeCl_3 \cdot 6H_2O$)

line 34, "($Fe(NO_3)_3 \cdot 9H_2O$)" should be --($Fe(NO_3)_3 \cdot 9H_2O$)-- line 44, "($NaH_2PO_4 \cdot H_2O$)" should be --($NaH_2PO_4 \cdot H_2O$)-- line 46, "($Na_2SeO_3 \cdot 5H_2O$)" should be --($Na_2SeO_3 \cdot 5H_2O$)-- line 61, "L-arginin . HCl" should be --L-arginine $\cdot$ HCl-- lines 63 & 64, "L-cystine . 2HCl" should be --L-cystine $\cdot$ 2HCl-- line 65, "L-histidine . HCl . $H_2O$" should be --L-histidine $\cdot$ HCl $\cdot$ $H_2O$-- line 68, "L-lysine . HCl" should be --L-lysine $\cdot$ HCl--

Column 6, line 12, "L-asparagine . $H_2O$" should be --L-asparagine $\cdot$ $H_2O$-- line 19, "L-asparagine . $H_2O$" should be --L-asparagine $\cdot$ $H_2O$-- line 41, "pyridoxal . HCl" should be --pyridoxal $\cdot$ HCl-- line 44, "thiamine . HCl" should be --thiamine $\cdot$ HCl--

Column 7, line 6, "not" should be --noted--

UNITED STATES PATENT AND TRADEMARK OFFICE
CERTIFICATE OF CORRECTION

PATENT NO. : 4,560,655

DATED : December 24, 1985

INVENTOR(S) : Paul E. Baker

It is certified that error appears in the above-identified patent and that said Letters Patent is hereby corrected as shown below:

Column 9, line 5, "serim-containing" should be --serum-containing-- line 18, "Calif.," should be --Calif.-- line 27, "as" should be --has-- line 60, "(FeCl$_3$ . 6H$_2$O)" should be --(FeCl$_3 \cdot$ 6H$_2$O)--

Column 10, line 36, "Fe(NO$_3$)$_3$ . 9H$_2$O)" should be --Fe(NO$_3$)3$\cdot$9H$_2$O-- line 39, "NaH$_2$PO$_4$ . H$_2$O" should be --NaH$_2$PO$_4 \cdot$ H$_2$O-- line 44, "L-Arginine . HCl" should be --L-Arginine$\cdot$HCl-- line 45, "L-Cystine . 2HCl" should be --L-Cystine$\cdot$2HCl-- line 47, "L-Histidine . HCl . H$_2$O" should be L-Histidine$\cdot$HCl$\cdot$H$_2$O-- line 50, "L-Lysine . HCl" should be --L-Lysine$\cdot$HCl--

Column 12, line 7, "cystine . HCl solution);" should be --(cystine$\cdot$HCl solution);-- line 47, "Fe(NO$_3$)$_3$ . 9H$_2$O" should be --Fe(NO$_3$)$_3\cdot$ 9H$_2$O-- line 51, "NaH$_2$PO$_4$ . H$_2$O" should be --NaH$_2$PO$_4\cdot$H$_2$O-- line 54, "L-Arginine . HCl" should be --L-Arginine$\cdot$HCl-- line 55, "L-Cystine . 2HCl" should be --L-Cystine$\cdot$2HCl--

UNITED STATES PATENT AND TRADEMARK OFFICE
CERTIFICATE OF CORRECTION

PATENT NO. : 4,560,655

DATED : December 24, 1985

INVENTOR(S) : Paul E. Baker

It is certified that error appears in the above-identified patent and that said Letters Patent is hereby corrected as shown below:

Column 12, line 58, "L-Histindine . HCl . $H_2O$" should be --L-Histindine•HCl•$H_2O$-- line 61, "L-Lysine . HCl" should be --L-Lysine • HCl-- line 68, "Pyridoxal . HCl" should be --Pyridoxal• HCl-- line 7, "Thiamine . HCl" should be --Thiamine • HCl--

Column 17, line 39, "L-arginine . HCL" should be --L-arginine • HCl--
(Claim 8, line 3)

Column 17, line 41, "L-histidine . HCl . $H_2O$" should be --L-histidine • HCl • $H_2O$--
(Claim 8, line 5)

Column 17, line 42, "L-lysine . HCl" should be --L-lysine • HCl--
(Claim 8, line 6)

Column 17, line 55, "D-calcium" should be --D-Calcium--
(Claim 11, line 3)

UNITED STATES PATENT AND TRADEMARK OFFICE
CERTIFICATE OF CORRECTION

PATENT NO. : 4,560,655

DATED : December 24, 1985

INVENTOR(S) : Paul E. Baker

It is certified that error appears in the above-identified patent and that said Letters Patent is hereby corrected as shown below:

Column 17, line 57, "thiamine . HCl" should be --thiamine • HCl--
(Claim 11, line 5)

Column 19, line 1, "acids" should be --acid--
(Claim 20, line 6)

Signed and Sealed this

Twenty-second Day of July 1986

[SEAL]

Attest:

DONALD J. QUIGG

Attesting Officer     Commissioner of Patents and Trademarks